(12) United States Patent
Brachman

(10) Patent No.: US 11,816,733 B1
(45) Date of Patent: Nov. 14, 2023

(54) TOKENIZATION OF SOCIAL IMPACT ON THE BLOCKCHAIN AND RELATED METHODS

(71) Applicant: The Joan and Irwin Jacobs Technion-Cornell Institute, New York, NY (US)

(72) Inventor: Rebecca Brachman, New York, NY (US)

(73) Assignee: THE JOAN AND IRWIN JACOBS TECHNION-CORNELL INSTITUTE, New York, NY (US)

(*) Notice: Subject to any disclaimer, the term of this patent is extended or adjusted under 35 U.S.C. 154(b) by 0 days.

(21) Appl. No.: 16/718,567

(22) Filed: Dec. 18, 2019

Related U.S. Application Data

(60) Provisional application No. 62/781,199, filed on Dec. 18, 2018.

(51) Int. Cl.
| | | |
|---|---|---|
| G06Q 40/06 | (2012.01) | |
| H04L 9/06 | (2006.01) | |
| H04L 9/00 | (2022.01) | |
| G16H 70/40 | (2018.01) | |

(52) U.S. Cl.
CPC ............ *G06Q 40/06* (2013.01); *G16H 70/40* (2018.01); *H04L 9/0637* (2013.01); *H04L 9/0643* (2013.01); *H04L 9/50* (2022.05)

(58) Field of Classification Search
CPC ..... G06Q 40/06; H04L 9/0637; H04L 9/0643; H04L 2209/38; G16H 70/40
USPC ............................................................. 705/35
See application file for complete search history.

(56) References Cited

U.S. PATENT DOCUMENTS

| | | | |
|---|---|---|---|
| 9,990,418 B1 | 6/2018 | Rogers | |
| 10,839,936 B2* | 11/2020 | Hu et al. | ............... G16B 5/00 |
| 2014/0046736 A1* | 2/2014 | Sanders | ............... G06Q 40/06 |
| | | | 705/12 |

(Continued)

FOREIGN PATENT DOCUMENTS

WO       2018164401 A1       9/2018

OTHER PUBLICATIONS

Syminvest, Blockchain Smart Contracts Could Shape Future of Impact Investing, Jan. 29, 2018, Symbiotics SA, syminvest@symbioticsgroup.com (Year: 2018).*

(Continued)

*Primary Examiner* — Scott C Anderson
*Assistant Examiner* — George N. Proios
(74) *Attorney, Agent, or Firm* — M&B IP Analysts, LLC

(57) ABSTRACT

Systems and methods for tokenization of social good. A disclosed method includes encoding a smart contract based on a plurality of project parameters for a social impact project, wherein the smart contract includes at least one self-executing code; and issuing a token to a user based on an investment made by the user, wherein issuing the token to the user further comprises recording a first transaction on a blockchain indicating that the user owns the token, wherein each of the at least one self-executing code is configured to record a second transaction on the blockchain based on the plurality of project parameters and data related to progress of the social impact project, wherein each second transaction includes a respective transfer of funds via the token issued to the user.

18 Claims, 9 Drawing Sheets

(56) References Cited

U.S. PATENT DOCUMENTS

| | | | |
|---|---|---|---|
| 2015/0095262 A1* | 4/2015 | McIntosh et al. | G06Q 40/06 |
| | | | 705/36 |
| 2017/0300876 A1* | 10/2017 | Musiala, Jr. et al. | G06Q 20/06 |
| 2018/0293650 A1* | 10/2018 | Beck | G06Q 40/04 |
| 2018/0341910 A1* | 11/2018 | Broveleit | G06Q 10/08 |
| 2019/0080402 A1* | 3/2019 | Molinari et al. | G06Q 40/04 |
| 2019/0147505 A1* | 5/2019 | Blass | G06Q 30/02 |
| 2019/0340689 A1* | 11/2019 | Gordon et al. | G06Q 40/04 |

OTHER PUBLICATIONS

Doug Galen, et al., Blockchain for Social Impact Moving Beyond the Hype, Apr. 11, 2018, Stanford Graduate School of Business Center for Social Innovation, RippleWorks. (Year: 2018).*

* cited by examiner

TOKENIZATION OF SOCIAL IMPACT ON THE BLOCKCHAIN AND RELATED METHODS

CROSS-REFERENCE TO RELATED APPLICATIONS

This application claims the benefit of U.S. Provisional Application No. 62/781,199 filed on Dec. 18, 2018, the contents of which are hereby incorporated by reference.

TECHNICAL FIELD

The present disclosure relates generally to tokenization of social impact or social good on a blockchain and related methods for funding social impact or social good projects that generate social benefit but may not otherwise be funded without improvements to technology and methodology.

BACKGROUND

Frequently, the market fails to capture the value of social good. New financial instruments are beginning to emerge to capture these externalities (for example, social impact bonds, income share agreements, and micropatronage). In a few cases, these new technologies are scalable (for example, the internet and smart phone-enabled crowdfunding). However, in most cases, a value-capturing technology has yet to be invented to incentivize social good—particularly where the outcomes are not guaranteed (i.e., not de-risked).

For example, social impact bond is a contract typically made with a governing entity or otherwise an actor in the public sector. Pursuant to this contract, an entity invests in a social good activity and, in exchange, becomes entitled to a reward based on the savings achieved by the social good activity. Because the reward is based on the actual savings achieved, the investing entity only receives a reward if the social good activity successfully achieves its intended result.

Due to the contingency inherent in social impact bonds, attracting investors can be challenging. In particular, projects which have a low likelihood of success or which require a large investment may be deemed too risky to invest in. Thus, techniques for attracting investors are desirable.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for tokenization of social good via blockchain. The method comprises: encoding a smart contract based on a plurality of project parameters for a social impact project, wherein the smart contract includes at least one self-executing code; and issuing a token to a user based on an investment made by the user, wherein issuing the token to the user further comprises recording a first transaction on a blockchain indicating that the user owns the token, wherein each of the at least one self-executing code is configured to record a second transaction on the blockchain based on the plurality of project parameters and data related to progress of the social impact project, wherein each second transaction includes a respective transfer of funds via the token issued to the user.

Certain embodiments disclosed herein also include a non-transitory computer readable medium having stored thereon causing a processing circuitry to execute a process, the process comprising: encoding a smart contract based on a plurality of project parameters for a social impact project, wherein the smart contract includes at least one self-executing code; and issuing a token to a user based on an investment made by the user, wherein issuing the token to the user further comprises recording a first transaction on a blockchain indicating that the user owns the token, wherein each of the at least one self-executing code is configured to record a second transaction on the blockchain based on the plurality of project parameters and data related to progress of the social impact project, wherein each second transaction includes a respective transfer of funds via the token issued to the user.

Certain embodiments disclosed herein also include a system for tokenization of social good via blockchain. The system comprises: a processing circuitry; and a memory, the memory containing instructions that, when executed by the processing circuitry, configure the system to: encode a smart contract based on a plurality of project parameters for a social impact project, wherein the smart contract includes at least one self-executing code; and issue a token to a user based on an investment made by the user, wherein issuing the token to the user further comprises recording a first transaction on a blockchain indicating that the user owns the token, wherein each of the at least one self-executing code is configured to record a second transaction on the blockchain based on the plurality of project parameters and data related to progress of the social impact project, wherein each second transaction includes a respective transfer of funds via the token issued to the user.

Certain embodiments also include a method for tokenization of social good. The method comprises: encoding a smart contract based on a plurality of project parameters for a social impact project, wherein the smart contract includes at least one self-executing code; and issuing a token to a user based on an investment made by the user, wherein issuing the token to the user further comprises recording the investment, wherein each of the at least one self-executing code is configured to provide funds to the user via the token based on the plurality of project parameters and data related to progress of the social impact project.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
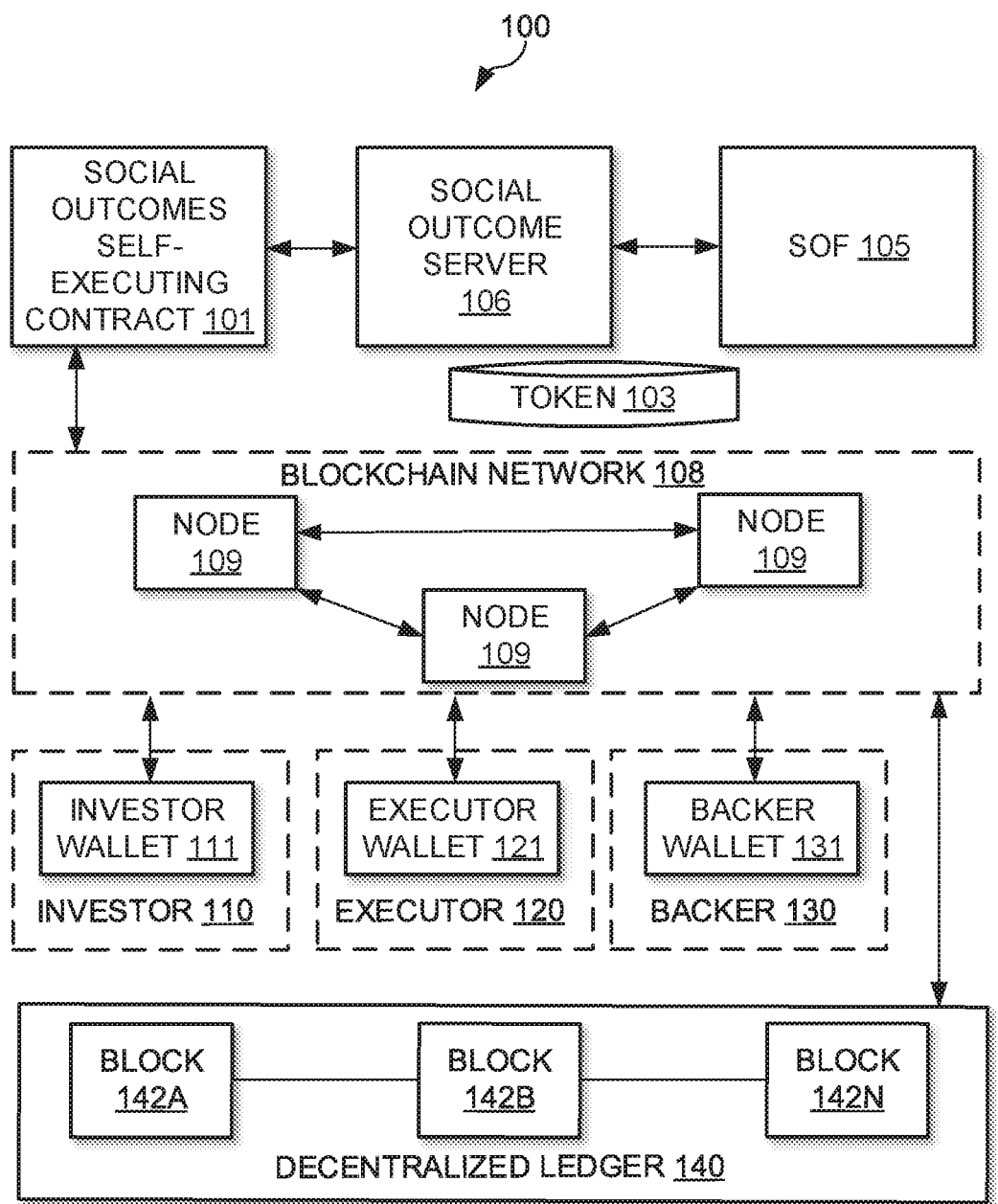
FIG. 1 illustrates an example of a system for tokenization of social impact or social good using blockchain technology according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The disclosure relates to tokenization of social impact or social good on a blockchain and related methods for funding projects that generate social benefit. For example, the blockchain tokenizes social good, encouraging investment in activities that would otherwise not get funded through conventional means but that benefit society (these activities will be referred to as "social impact projects"). Investors that fund social impact projects may be issued a cryptocurrency token based on the investment, which is written to a decentralized ledger. The ledger provides secure and immutable proof of ownership of the token. Investments may be directed to a social outcome fund (SOF), which funds one or more social impact projects. In some instances, the SOF and the token will be specific to a social impact project (in which case an investor may select particular social impact projects to fund) or may be generic for multiple social impact projects. More generally, implementing the SOF may be seen as a method for funding and monetizing social impact projects that generate social good but may not otherwise be funded. Technology and methods that facilitate the foregoing will be described with reference to the figures. Various examples used throughout will refer to a social fund relating to funding discovery of novel indications for generic or drugs for convenience. Other social impact projects that generate other social good may be funded as well.

The technology described herein transforms social impact and social good into commodities and/or assets that may be securitized, which in some cases may also be fungible (e.g., units of clean air). This renders social impact and social good transactable and introduces liquidity—and ultimately potentially market efficiency—to a space that capitalism and market forces have been hitherto unable to address. In this manner, this technology enables the funding and execution of a class of social impact and social good projects that traditional markets have previously been unable to fund.

Additionally, the disclosed embodiments allow for providing value in exchange for contributions to social good in a manner that ensures anonymity of users, i.e., of investors, payers, evaluators, or a combination thereof. Specifically, transactions recorded on the blockchain in accordance with the disclosed embodiments provide assurance of rewards through self-executing contracts upon completion of milestones without requiring identification of entities evaluating the social impact, thereby preventing collusion that might cause investors or payers to lose confidence in the terms of the smart contract and, therefore, to be disincentivized to participate.

The disclosed embodiments also provide techniques for ensuring accurate enforcement of the smart contract. More specifically, electronic messages including indications of progress on a social impact project, transfers of funds, or both may be recorded as transactions on a blockchain and distributed across nodes of a blockchain network. The distributed recordation provides assurance to users that the records of progress and transfers of funds cannot be later modified. Further, the transactions recorded on the blockchain may be verified prior to recordation, thereby ensuring, for example, that terms of the smart contract enforced via self-executing code of the smart contract are enforced based on accurate data.

The disclosed embodiments also provide enabling technology for social impact and social good contracts that require distributed and/or large numbers of participating agents. For example, the disclosed embodiments allow for effective implementation of a project backed by the property value of thousands of individual buildings, or a project in which air quality readings are automatically downloaded from consumer-owned monitors across thousands of households.

Beyond its colloquial usage, "social impact" may refer to change (A)—positive, negative, or otherwise—often created by an intervention. The value of this change can be represented as a token. Examples may include: curing or preventing disease (positive impact), decreasing recidivism (positive impact), generating pollution (negative impact), and/or other forms of social impact. Quantification of "social impact" may be derived from existing forms of measurable value such as savings, secondary savings, revenue, or asset appreciation; derived from novel forms of measurable value; determined by arbitrary metrics; one or more other quantification techniques; or a combination thereof. Verification that a given amount of "social impact" has been achieved could be determined on a case-by-case basis by a third-party auditor (such as an agency, database, other information source or predetermined entity, or a combination thereof). Alternatively, template smart contracts could encode standardized metrics, automated milestone-triggered payments (reporting of which could be regulated by "the platform" or by the FCC), or both, thereby establishing standardization in the sector. Value of a given token may be 1:1 with the "social impact" it represents, or determined by other means of price setting such as, but not limited to, a market (ala stock pricing).

"Social good" may refer to a good or asset itself, such as clean air, which may have a finite quantity that can be represented as tokens. Value of a given token may be 1:1 with the "social good" it represents (ala commodities), or determined by other means of price setting, such as a market (ala stock pricing). "Social impact" and "social goods" are often externalities in the current economy; the value of some of these externalities can be captured by the tokenization technology disclosed herein.

FIG. 1 illustrates an example of a system 100 for tokenization of social impact or social good using blockchain technology according to an embodiment. System 100 may include a social outcomes self-executing contract 101 (also referred to herein as "smart contract 101"), tokens 103, a social outcome fund 105 (or "SOF 105"), a blockchain network 108, a social outcome server 106, various wallets (111, 121, 131) of various entities (investor 110, executor 120, backer 130), a decentralized ledger 140, other components, or a combination thereof. The social outcome server 106 may be programmed to execute management of the SOF 105. For example, the social outcome server 106 may be operated by an operator of the SOF 105 and may register or otherwise set up social impact projects and corresponding smart contract 101.

Smart Contract

Smart contract 101 may include self-executing computer code that automatically carries out the operational terms of an agreement, between various parties (such as investors 110, executors 120, backers 130, other parties, or a combination thereof). For example, the terms may be written into and executed by the lines of code. The code may be stored across the distributed nodes 104 of the decentralized blockchain network 108. The smart contract 101 may automatically receive data from various sources such as investors 110, executors 120, backers 130, other entities, or a combination thereof, and programmatically implement decisions that are automatically executed based on the received data.

Tokens

A token 103 may include crypto-tokens issued to an investor 110 or others. The tokens 103 may be issued as part of an Initial Coin Offering ("ICO") for providing proof of funding by an investor into the SOF 105. Each token 103 may be issued specifically for a social impact project or may be issued generally for use in all social impact projects and other uses. In some implementations, the token 103 may be implemented as a cryptocurrency. A cryptocurrency is a digital currency that uses cryptography for security and for which transactions are typically recorded to a blockchain. As such, tokens 103 may serve as a digital currency, but can also be programmed to include additional functionality, such as proof of investment and other functionality.

In an embodiment, each token has a value that may be backed by value of one or more external entities or assets (i.e., entities or assets whose value is not directly connected to the smart contract or tokens). As non-limiting examples, such external entities may include tangible items or commodities (e.g., gold), savings achieved by social impact projects (e.g., reduction in healthcare costs for a country), value added due to social impact projects (e.g., an increase in value to real estate caused by a social impact project), novel commodities (e.g., cloud cover), or a combination thereof.

Recordation of ownership of the tokens 103 may occur via a block 142 in the decentralized ledger 140. Typically, this is implemented using public key/private key encryption. A user (such as investor 110, executor 120, backer 130) may be assigned with a public key that is published to the blockchain network 108 and a private key that is held by the user in secret. The public key may publicly identify the user and may be stored in association with the user's wallet (111, 121, 131), which is associated with a balance of tokens 103, other value, or both, owned by the user. The user may sign transactions using the private key. For example, the user may encrypt a transaction using the user's private key. Only the user's public key associated with the user's private key can decrypt data encrypted with the private key. The blockchain network 108 may verify the identity of the user (and that the user indeed signed the transaction) by decrypting the transaction using the user's public key. In some instances, tokens 103 may be transferred between users, such as through their respective wallets (111, 121, 131). As such, a token 103 may be traded and exchanged mediated through the blockchain.

The Social Outcome Fund—Project Specific or Generalized Pool of Funds

The SOF 105 may include funds received from investors 103 or others. Funds from the SOF 105 may be provided to one or more social impact projects, such as to executors 120 that work toward providing social good and completing a social impact project. An SOF 105 may be project-specific or a generalized fund for all projects. For example, in some instances, one SOF 105 may be specific for a first social impact project while another SOF 105 may be specific for a second social impact project. In these instances, an investor 110 may select a particular SOF 105 in which to invest. Alternatively, a single SOF 105 may serve as a general fund for funding multiple social impact projects. In these instances, operators of the SOF 105 may select specific social impact projects in which to invest on behalf of the investor 110. In either instance, the investor may be issued one or more tokens 103 based on the amount of the investment. In some instances, an investor 110 donates funds to the SOF 105 and not expect a return on the investment. In these instances, the investor 110 may relinquish all or portion of the value of the tokens 103 back to the SOF 105 or other holder of tokens. Any returns from these "donated" tokens 103 may be provided back to the SOF 105 for funding social impact projects.

The Blockchain Network

The blockchain network 108 may include multiple nodes 109 connected to one another, such as using a peer-to-peer connection. Each node 109 may execute a blockchain agent (such as blockchain software) to access the decentralized ledger 140 and communicate with one another. In some instances, users of the system may be provided with blockchain agents for execution at their devices. For instance, various users or system components may be assigned with a blockchain wallet application (illustrated as wallets 111, 121, 131). Each wallet may hold a value of tokens 103. To hold tokens 103, each wallet may be assigned with a public key and a private key. The private key may be held in secret by each wallet while the public key may publicly available to identify the corresponding wallet. The public key may be used to identify tokens 103 held by a user that holds the corresponding private key. A given wallet may "hold" tokens 103 based on an association of the tokens 103 with the wallet's public key recorded on the decentralized ledger 140.

Blockchain transactions may include electronic messages that are sent from a sender to the blockchain network 108. Such messages may include an indication of progress of a social impact project (such as achievement of a milestone), an indication of an amount of funds to be transferred (such as an investment amount from an investor), other messages, or a combination thereof, for processing on the blockchain. For example, all or a portion of the tokens 107 may be transferred between wallets by generating a blockchain transaction that identifies a recipient's public key and a transfer amount. The blockchain transaction may be signed by the sender, and broadcast and relayed to various nodes 109 in the blockchain network 108 in a peer-to-peer manner. The blockchain network 108 may verify the transaction by using the sender's public key to verify that the sender actually signed the transaction. Other consensus validation processing may be performed as well.

Once validated, the transaction may be accepted by consensus and written to a block 142, which is added to the decentralized ledger 140. The transaction may be grouped with other transactions into a single block 142. For Proof-of-Work implementations, the transaction(s) may be hashed together with a nonce and the hash of the previous block 142 until a hash value below a threshold value is found (as set by the blockchain network 108). Various nodes 109 may compete to add blocks 142 to the decentralized ledger 140. As a reward for doing so, operators of nodes 109 may be provided with a reward in the form of a transaction fee, which may be paid for by the SOF 105, investors 110, executors 120, backers 130, others, or a combination thereof. For Proof-of-Stake implementations, the transaction(s) may be hashed together by nodes 109 that hold a certain number or value of tokens 107 (thereby proving their stake in the system).

The Decentralized Ledger

The decentralized ledger 140 may include a series of blocks of data 142A-N (where N is an integer having a value of 1 or greater) that are chained together. For example, each block 132 may be identified by a hash. Each block 142 may include a reference to a previous block's hash. In this manner, the blocks of data may be chained together. An example of a decentralized ledger is described in the white paper "Bitcoin: A Peer-to-Peer Electronic Cash System," by Satoshi Nakamoto (bitcoin.org), the contents of which are hereby incorporated by reference. Other blockchain platform technologies may be used as well, such as the Ethereum platform, described in the white paper, "Ethereum Specification" (https://github.com/ethereum/wiki/wiki/White-Paper), the contents of which are hereby incorporated by reference. It should be noted that the foregoing examples of decentralized ledgers do not include various features disclosed herein that facilitate social impact and are used as examples of distributed ledgers. Full or partial copies of the decentralized ledger 140 may be stored at or by each node 109.

Stakeholders

Various individuals or entities may use the systems and methods described herein to promote social good. For instance, investors 110 may invest in the SOF 105 to promote social good and/or obtain a return on their investment, executors 120 may work on social impact projects to benefit society and/or achieve profits, backers 130 may enjoy benefits such as cost savings resulting from the projects and pass along all or portion of the benefits or savings back to the SOF 105 for distribution as returns back to the investors. An investor 110 may include one or more individuals, entities, or a combination thereof, that invest capital that is used to fund the execution of a project. An executor 120 may include one or more individuals, entities, or a combination thereof that receive funding to ideate, plan, or execute a project that causes a positive social outcome and/or creates or supports common good. A backer 130 may include one or more individuals, entities, or a combination thereof that either save money, gain money, or volunteer an arbitrary bounty and/or prize when a social outcome is achieved by a project. Backers may agree to contribute fiat currency, cryptocurrency (like Bitcoin or Ether) other than tokens 103, another currency or value, or a combination thereof. Backers 130 may include, but are not limited to, hospitals, government agencies, insurance companies, and other individuals or entities that obtain a benefit from the social impact project. In some instances, this benefit may be quantifiable, such as when use of a generic or otherwise less expensive drug can replace or augment the use of a brand or otherwise more expensive drug. This discovery may lower the cost of treating diseases, which may have a direct impact on the profitability of an insurance company. In these instances, the smart contract 101 may specify that a percentage of the quantifiable savings be provided as a return to the SOF 105. In other instances, this benefit may not be quantifiable, in which case the backers 130 may agree to generally provide funds when a social impact project is started and/or when milestones are achieved.

Investors 110, executors 120, backers 130, or capital may also be obtained—or social good projects may be executed—through crowd-sourcing. Example social impact projects enabled by this technology include, but are in no way limited to, share-in-savings and share-in-revenue-backed infrastructure projects (such as national water purification and distribution systems in developing nations); climate change mitigation projects with local governments or private real-estate holders as backers (such as a share-in-property-value-backed project to prevent coastal land loss); share-in-prize-based community-investor funded student participation in academic competitions; a "clean air economy" or "clean water economy" composed of a finite number of tokenized "common good" units (clean air and clean water, respectively) which captures the negative externality of pollution and the positive externality of carbon sequestration; and/or other social impact projects enabled and/or executed through crowd-sourcing.

Tokenizing Investments for Social Good

Figure 2:
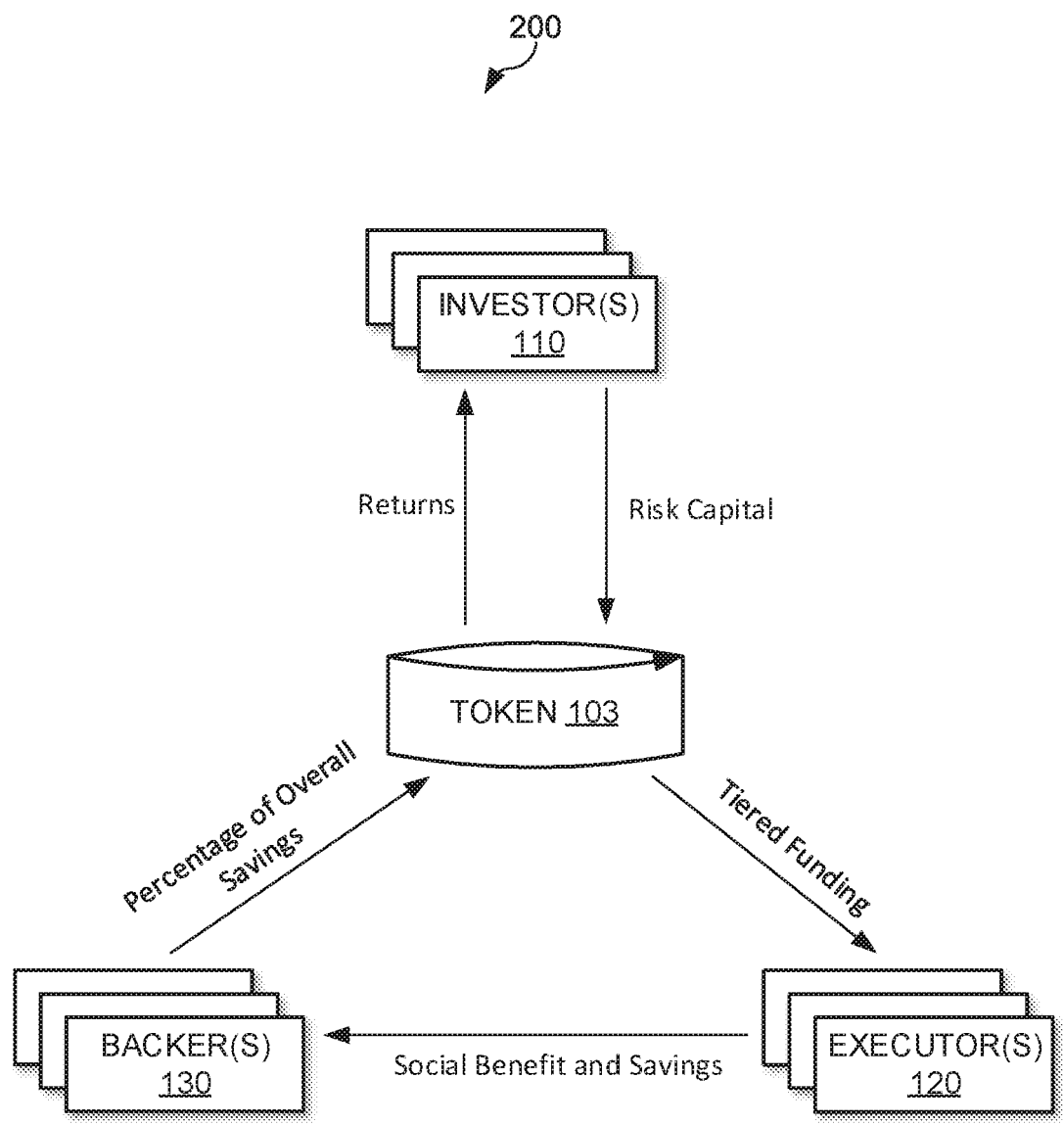
FIG. 2 illustrates a schematic diagram of tokenization of social impact or social good using blockchain technology, according to an implementation of the disclosure.

FIG. 2 illustrates a schematic diagram 200 of tokenization of social impact or social good using blockchain technology, according to an implementation of the disclosure. Investors 110 may provide risk capital in exchange for one or more tokens 103. The risk capital may include fiat currency, cryptocurrency (like Bitcoin or Ether) other than tokens 103, another currency/value, or a combination thereof. The risk capital may be used to fund the SOF 105. Funds from the SOF 105 may be provided to executors 120. Such funding may be tiered based on achievement of milestones. As will be described with respect to FIG. 3, funding may be automatically provided from the SOF 105 to the executors 120 by execution of the smart contract 101 for the social impact project. The executors 120 may use the funds to conduct research or otherwise product social outcomes that are beneficial to society. For instance, the executors 120 may research and discover new uses of existing drugs that are off-patent. This type of research can greatly benefit society, as treatments for disease using relatively inexpensive (off-patent) drugs may be discovered that would not otherwise be discovered since, due to the relative unenforceability of method-of-use pharmaceutical patents as a result of off-label prescribing, pharmaceutical companies tend to concentrate research and development on discovery of novel drug compounds (not novel uses of existing drugs).

Backers 130 may agree to pass along a percentage of savings resulting from the social benefit and savings back to the SOF 105, which may be distributed back to investors 110 as returns on investment. Such returns may be based on the amount of investment made by the investors into the SOF 105, as recorded in their ownership of tokens 103. It should be noted that some or all of the fund transfers may be made automatically via execution of the smart contract 101 for the social impact project, via the SOF 105 as a whole, or both. It should be further noted that such fund transfers may be made via various wallets disclosed herein. Furthermore, in some implementations, the funds themselves may be in the form of tokens 103, other currencies, or a combination thereof.

Figure 3:
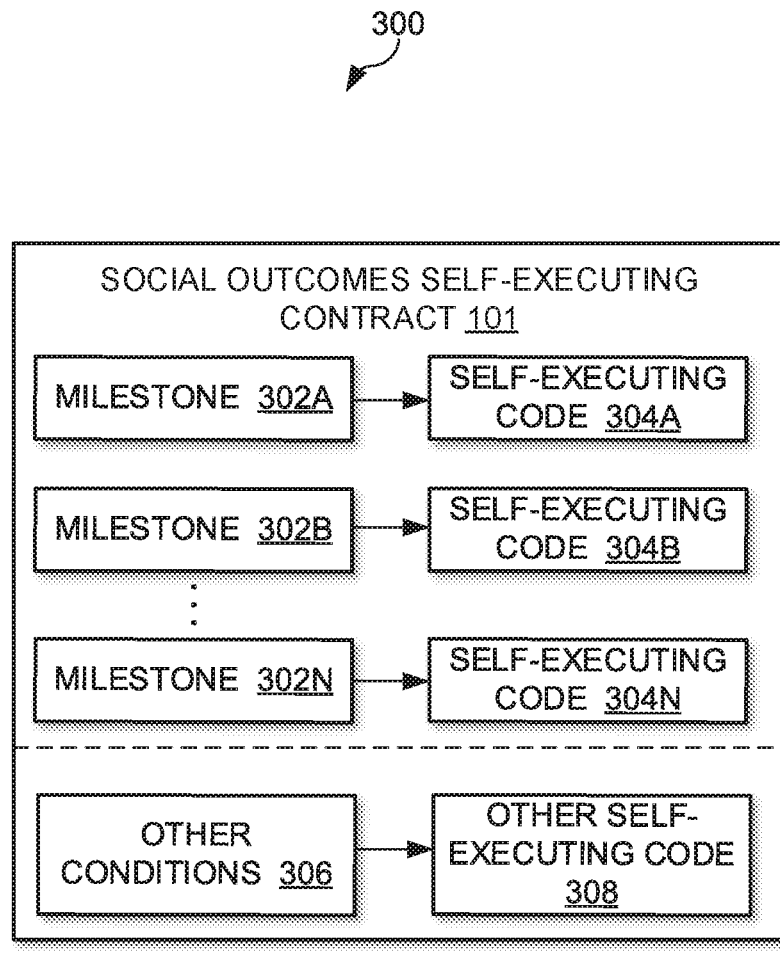
FIG. 3 illustrates a schematic diagram of a smart contract having self-executing code for tokenizing social impact or social good according to an embodiment.

FIG. 3 illustrates a schematic diagram 300 of a smart contract 101 having self-executing code for tokenizing social impact or social good according to an embodiment. The smart contract 101 may be encoded with multiple milestones 302 (302A-N, where N is an integer having a value of 1 or greater), other conditions 306, or a combination thereof. Each milestone 302 may have a corresponding self-executing code 304 (304A-N) that may be automatically executed by the blockchain network 108 (e.g., by one or more nodes 104). For example, each milestone 302 may be validated according to the corresponding self-executing code 304. Any associated fund transfers or payments may be automatically made accordingly. For example, if an executor 120 broadcasts that it has completed a particular milestone of a social impact project, the smart contract 101 may be consulted to determine any next actions to take, such as providing funds automatically to the wallet 121 of the executor 120. In some instances, achievement of the milestone may be subject to verification, such as by a backer 130 or operator of the SOF 105. Other conditions 306 with corresponding self-executing code 308 may be encoded into the smart contract 101, such as when the SOF 105 was created.

Figure 4:
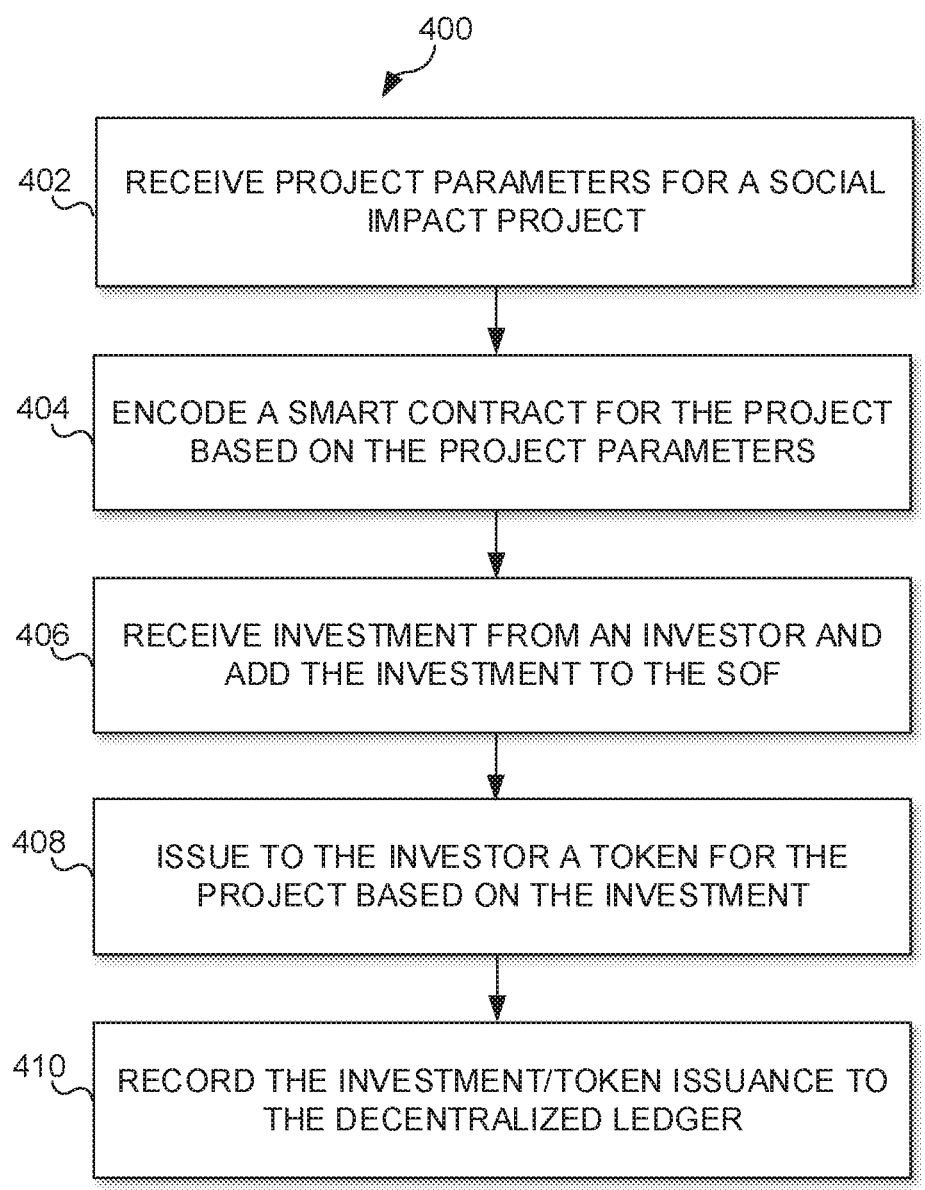
FIG. 4 illustrates an example of a process of issuing crypto-tokens recorded on the blockchain for social impact or social good according to an embodiment.

FIG. 4 illustrates an example of a process 400 of issuing crypto-tokens recorded on the blockchain for social impact or social good according to an embodiment. The operations of process 400 presented below are intended to be illustrative and, as such, should not be viewed as limiting. In some implementations, process 400 may be accomplished with one or more additional operations not described, and/or without one or more of the operations discussed. In some implementations, two or more of the operations may occur substantially simultaneously. The described operations may be accomplished using some or all of the system components described in detail above.

In an operation 402, process 400 may include receiving project parameters for a social impact project. For example, the project parameters may specify the goal of the project, project milestones, tiered funding, and/or other parameters that describe the project.

In an operation 404, process 400 may include encoding a smart contract, such as a smart contract 101, for the project based on the project parameters.

In an operation 406, process 400 may include receiving an investment from an investor 110 and adding the investment to the SOF 105. The investment may be received in the form of fiat currency, cryptocurrency other than tokens 103, other measure of value, or a combination thereof.

In an operation 408, process 400 may include issuing to the investor a token 103 for the social impact project based on the investment. In some instances, the token 103 is specific for the social impact project such that returns are based on the specific social impact project and not other projects funded by the SOF 105. In other instances, the token 103 is general to the SOF 105 such that returns are based on the entirety of projects funded by the general SOF 105.

In an operation 410, process 400 may include recording the investment and token ownership as a block 142 of the decentralized ledger 140. Recording blocks on the decentralized ledger is described herein.

Figure 5:
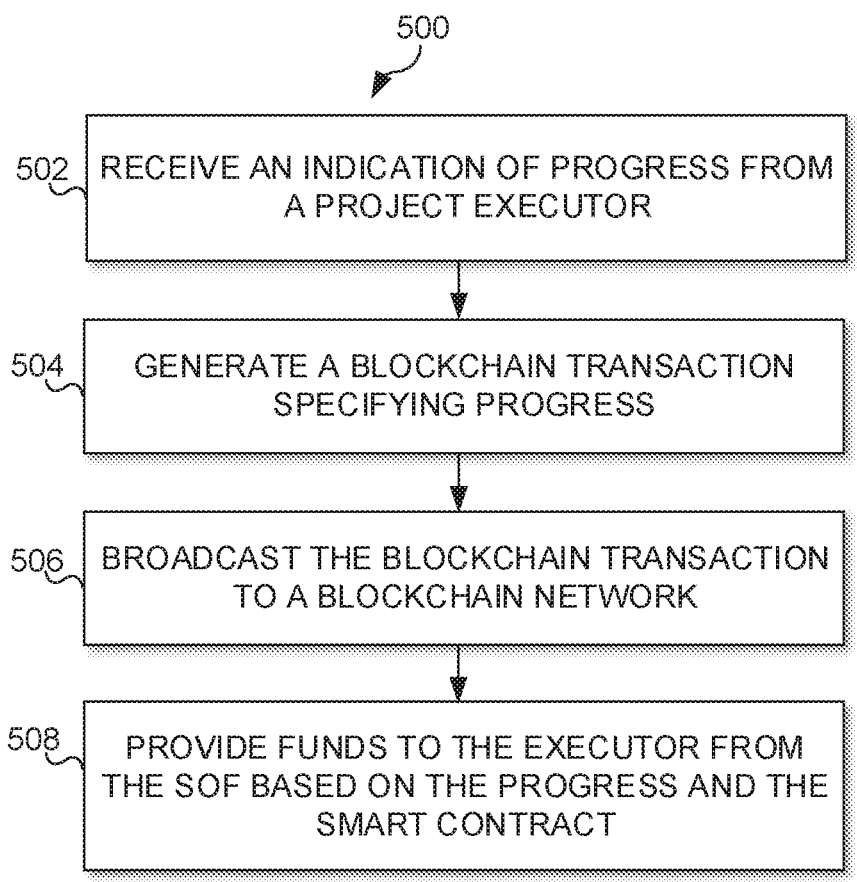
FIG. 5 illustrates an example of a process of providing milestone updates for automatically obtaining tiers of funding based on a smart contract according to an embodiment.

FIG. 5 illustrates an example of a process 500 of providing milestone updates for automatically obtaining tiers of funding based on a smart contract according to an embodiment. The operations of process 500 presented below are intended to be illustrative and, as such, should not be viewed as limiting. In some implementations, process 500 may be accomplished with one or more additional operations not described, and/or without one or more of the operations discussed. In some implementations, two or more of the operations may occur substantially simultaneously. The described operations may be accomplished using some or all of the system components described in detail above.

In an operation 502, process 500 may include receiving an indication of progress in a social impact project from an executor 120. For example, an executor 120 may use her wallet 121 to input achievement of a milestone in the social impact project.

In an operation 504, process 500 may include generating a blockchain transaction specifying the progress. For example, the wallet 121 may generate one or more messages that specifies that the milestone has been achieved. This milestone may be identified by a milestone identifier that was set up when the social impact project was created.

In an operation 506, process 500 may include broadcasting the blockchain transaction to the blockchain network 108. The blockchain network 108 may validate the transaction based on the public key of the executor 120 and may consult the smart contract 101 of the project to determine whether the milestone identifier is a valid milestone. Other validations may be performed as well.

In an operation 508, process 500 may include providing funds to the executor 120 from the SOF 105 based on the progress indication and terms of the smart contract 101. In some instances, such fund transfer may be made to the wallet 121 of the executor 120. For example, one or more nodes 104 of the blockchain network 108 may automatically execute the terms of the smart contract 101, and record the blockchain transaction, the transfer of funds to the decentralized ledger 140, or both.

Figure 6:
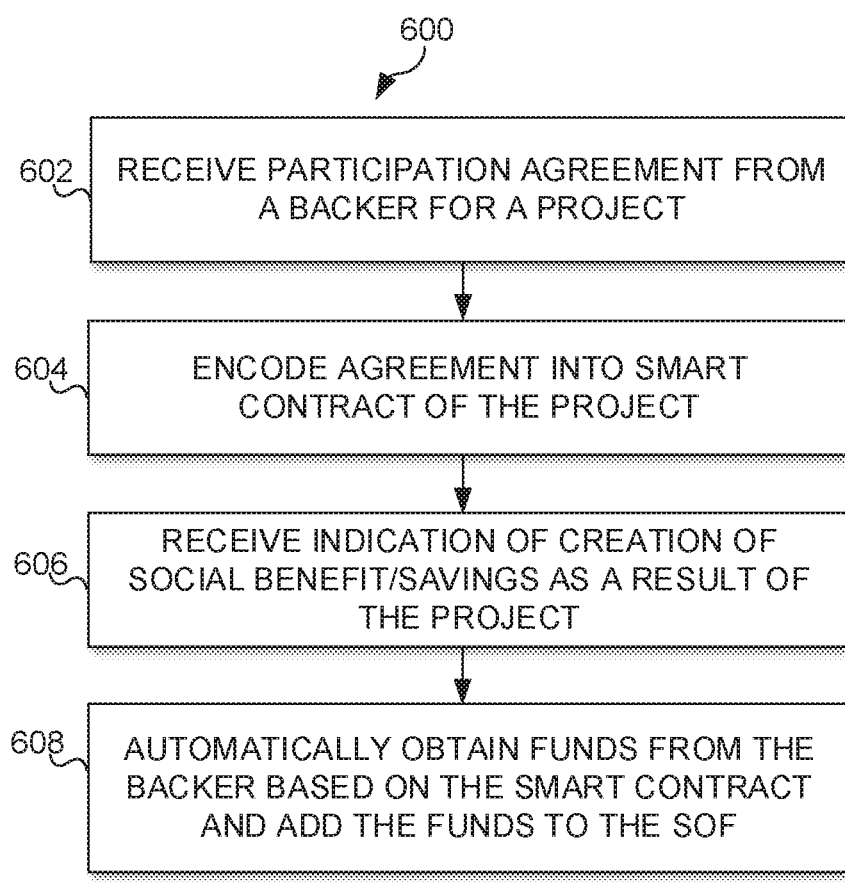
FIG. 6 illustrates an example of a process of automatically obtaining funds from backers according to the smart contract according to an embodiment.

FIG. 6 illustrates an example of a process 600 of automatically obtaining funds from backers according to the smart contract according to an embodiment. The operations of process 600 presented below are intended to be illustrative and, as such, should not be viewed as limiting. In some implementations, process 600 may be accomplished with one or more additional operations not described, and/or without one or more of the operations discussed. In some implementations, two or more of the operations may occur substantially simultaneously. The described operations may be accomplished using some or all of the system components described in detail above.

In an operation 602, process 600 may include receiving a participation agreement from a backer 130. The backer 130 may include entities that may benefit from cost savings and other efficiencies produced by the social impact project.

In an operation 604, process 600 may include encoding the terms of the participation agreement into the smart contract 101 for the social impact project. For instance, payments to be made from the backer 130 to the SOF 105 and the conditions under which such payment occurs may be encoded into the smart contract 101.

In an operation 606, process 600 may include receiving an indication of social benefit and/or cost savings as a result of the social impact project. For instance, the executor 120 and/or others may provide an indication that one or more milestones in connection with the discovery of a new use for a generic drug has been achieved. The new use may be associated with cost savings and/or an unquantifiable social good that was previously agreed to as an objective in the participation agreement.

In an operation 608, process 600 may include automatically obtaining funds from the backer(s) 130 based on the smart contract 101 and adding the funds to the SOF 105. These funds may be provided back to the investors 110 as a return in accordance with the number of tokens 107 held by the investors 110.

It should be noted that the various transactions and fund transfers described herein may take place through various users' wallets (111, 121, 131) and/or through other financial accounts.

Figure 7:
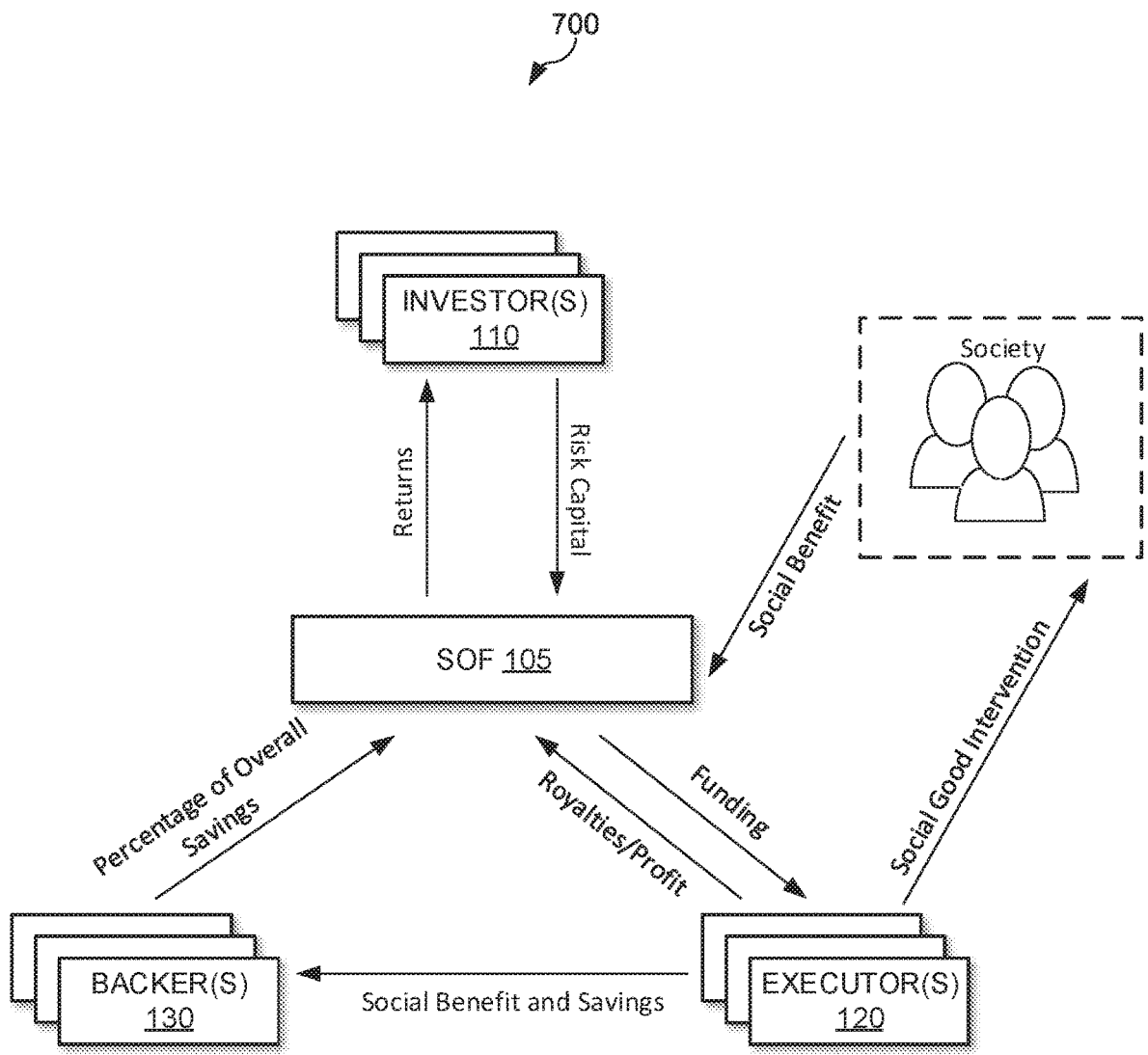
FIG. 7 illustrates a schematic diagram of a social outcome fund, according to an implementation of the disclosure.

FIG. 7 illustrates a schematic diagram 700 of a social outcome fund, according to an implementation of the disclosure. Common practice suggests that social problems can only be addressed by good will in the form of piecemeal government, nonprofit, or philanthropic interventions. This leaves many pressing and costly societal problems as largely unmet needs. However, a financial tool that captures the positive externalities of social good could solve this problem systematically by implementing the efficiency of a market-driven solution.

The SOF project embodied by the systems and methods described herein allows for creating and executing a hybrid structure that combines the core innovation of Pay-for-Success ("PFS") contracts with the flexibility and risk-tolerance of venture capital involvement. For example, the SOF 105 may include a portfolio of high-risk-high-return investments, similar to a venture-capital structure, which may distribute risk. Unlike a VC fund, however, the investments are not in companies in exchange for equity, but instead are in social good projects in exchange for partial ownership of an umbrella share-in-savings-like agreement with third party backers. Instead of mergers, acquisitions, or IPOs, these projects successfully "exit" by creating social good that results in quantifiable financial savings for the contract's backers.

In order to determine whether or not a project is successful, the SOF 105 works with the executors 120 and the backers 130 to agree upon outcomes-based metrics and milestones. The SOF 105 raises risk capital from investors, and then deploys this capital to multiple projects. Similar to a VC-fund like structure, the SOF 105 may deploy tiered and tranched capital to each project on a case-by-case basis determined by the stage of development of said project, with continued discretionary funding contingent on the project meeting pre-identified milestones. The backers 130, who benefit from the success of these projects, sign a share-in-savings-like contract with the SOF 105. In this contract, the backers 130 may agree to pay a percentage of the costs saved due to the success of projects back to the SOF 105. Thus, upon success of a project in the portfolio of the SOF 105, the backers 130 pay out a percentage of the savings that the project generates. Unlike PFS contracts, under the umbrella contract the backers 130 agree to back all of the projects in the portfolio of SOF 105 on a pro rata basis. This eliminates the inefficiencies of forming several traditional PFS contracts. Furthermore, combining this umbrella contract with a VC fund-like structure opens up a new class of assets that were previously un-fundable by traditional PFS contracts, including high-risk-high-reward social impact projects (SIPs), early-stage SIPs, long-term SIPs, small SIPs, basic research, prize- and revenue-backed SIPs, crowdsource-backed SIPs, multinational- and consortium-backed SIPs, SIPs executed by multiple and potentially competing executors, crowdsourced investment-funded SIPs, and/or other project funding mechanisms. Upon payment from the backers, the SOF 105 then distributes the carry similar to a traditional venture capital model.

Further, unlike social impact bonds (SIBs) or PFS contracts, the SOF 105 may deploy funds to multiple projects at different stages of development, providing subsequent follow-on funding as each project is de-risked. This allows the SOF 105 to develop early-stage and high-risk/high-reward projects that are currently un-fundable, such as basic research and drug development. Simultaneously, this structure of staged investment and diversification de-risks the SOF 105 overall. The SOF 105 may also differ from traditional PFS in that it will not be limited to a single rigid contract with a single backer. The SOF 105 may include backers from both the private and public sector, who will pay returns on a pro rata basis.

The SOF 105 may also be formed as a permanent capital structure. By creating a fluid umbrella contract under which each of the projects and backers can interact, the SOF 105 will expand the size of the market in which the PFS mechanism can act. By combining the PFS mechanism with a venture-capital-like structure, and ultimately securitizing social outcomes-based contracts, the SOF 105 unlocks a new asset class for impact investing. The fund could be structured as a traditional 2/20 fee structure with General Partners and Limited Partners, or otherwise, and includes the possibility of incentivizing executors of the projects by entitling them to a portion of the return.

In some implementations, SOF 105 may comprise an equity security model in which increments ("shares") of social outcomes-based investments can be bought or sold, thereby creating a market with liquidity. For example, a secondary market may be established to facilitate the purchase, sale, and/or exchange of tokens (e.g., tokens 103) issued specifically for a social impact project or other project implemented via or associated with the SOF 105. In some implementations, a platform, marketplace, and/or exchange may be established to facilitate the exchange of social outcomes-based projects. For example, a platform, marketplace, and/or exchange for the direct sale of investments into projects implemented via SOF 105 may be established. In an example implementation, a decentralized exchange may be established that facilitates the purchase, sale, or exchange of assets associated with projects implemented via the SOF 105. Transactions facilitated through the decentralized exchange may be recorded to a blockchain and accessible via a decentralized ledger. The assets purchased, sold, and/or exchanged may comprise template or standardized tokens, contracts, pre-contracted or pre-bundled backers, and/or other assets associated with SOF 105. In this vein, the systems and methods described herein may include the creation of a social impact and social good economy.

In some implementations, a platform, marketplace, and/or software may be created to facilitate the formation and establishment of social outcomes-based projects. This platform, marketplace, and/or software may include standard contracts; template contracts; pre-negotiated contracts with backers; standardized metrics and/or milestones; template metrics and/or milestones; evaluation of metrics and/or milestones; and/or verification of milestone attainment. This platform, marketplace, and/or software may facilitate backer consortiums; serve as a liaison/middleman (automated or otherwise) between projects, backers, and/or investors; and/or provide infrastructure for crowd-sourcing and/or crowd-funding. In some implementations, this may include additional tools to facilitate establishing or executing social outcomes-based projects, similar to how Amazon, Kickstarter, and the Facebook Platform provide services and tools to users including, but not limited to: payment infrastructure, distribution, marketing, and compliance support.

This fund structure differs significantly from classic "social impact investing," which can be found amongst firms such as, but not limited to, Goldman Sachs or BlackRock. "Social impact investing" is a class of investing characterized by a double bottom line in which the value of the social good created is often inversely proportional to the financial gain. As a result, "social impact investing" is incompatible with traditional venture capital (which expects 10× returns). "Social impact investing" instead attracts a niche group of investors, often investing in the form of offset against tax liability. Unlike "social impact investing", the SOF 105 model has a correlated, dependent, and proportional or "braided" bottom line: instead of competing, the amount of social good generated drives the rate of return.

The SOF 105 may be applied to many fields in which societal needs are unmet by traditional financial tools. The following use in a generic drug context is described for illustration and not necessarily limitation.

An unmet need in biomedical research relates to the challenge of repurposing generic drugs, which is currently considered un-fundable. The 'Problem of Repurposing' is a textbook example of the hitherto intractable class of market problems that are made solvable by the SOF 105. Drug development is an expensive and time-consuming process. It often takes more than 10 years and over a billion dollars to bring a single new drug to market. Moreover, it's highly risky; most investigational drugs (or "compounds") fail along the way due to insufficient safety or efficacy. Repurposing generics for new indications offers a cheaper, faster alternative. Generics are drugs that have previously been FDA approved and have since gone off patent. Generics can skip years of safety testing and are more likely than new compounds to be efficacious for other diseases due to redundancy in biology.

On average, approval takes half the time for repurposed generics, is 100-fold less expensive, and likelihood of success rises from 1:10,000 to 1:5. Though these new uses are technically patentable, the ability of doctors to prescribe "off-label" makes method-of-use patents impossible to enforce. As a result, despite clear social benefit, generic drugs are rarely repurposed due to insufficient financial incentives.

The SOF 105 may provide a market solution to this previously intractable problem by capturing the value of medical savings, pooling risk across drug assets, and staging investment. This novel structure creates an alternative up-front funding source for the research and development necessary to repurpose drugs for new disease indications. The SOF 105 may invest in multiple generics, each starting at various stages of preclinical and clinical development. This diversified portfolio de-risks the SOF 105, mitigating the residual risk of pharmaceutical development. Additionally, the potential massive savings from repurposing generics ensures that investors will see high returns on their initial investments.

The SOF 105 may simultaneously develop socially beneficial medical interventions and other beneficial societal outcomes, and be financially lucrative to those who invest in the SOF 105.

Figure 8:
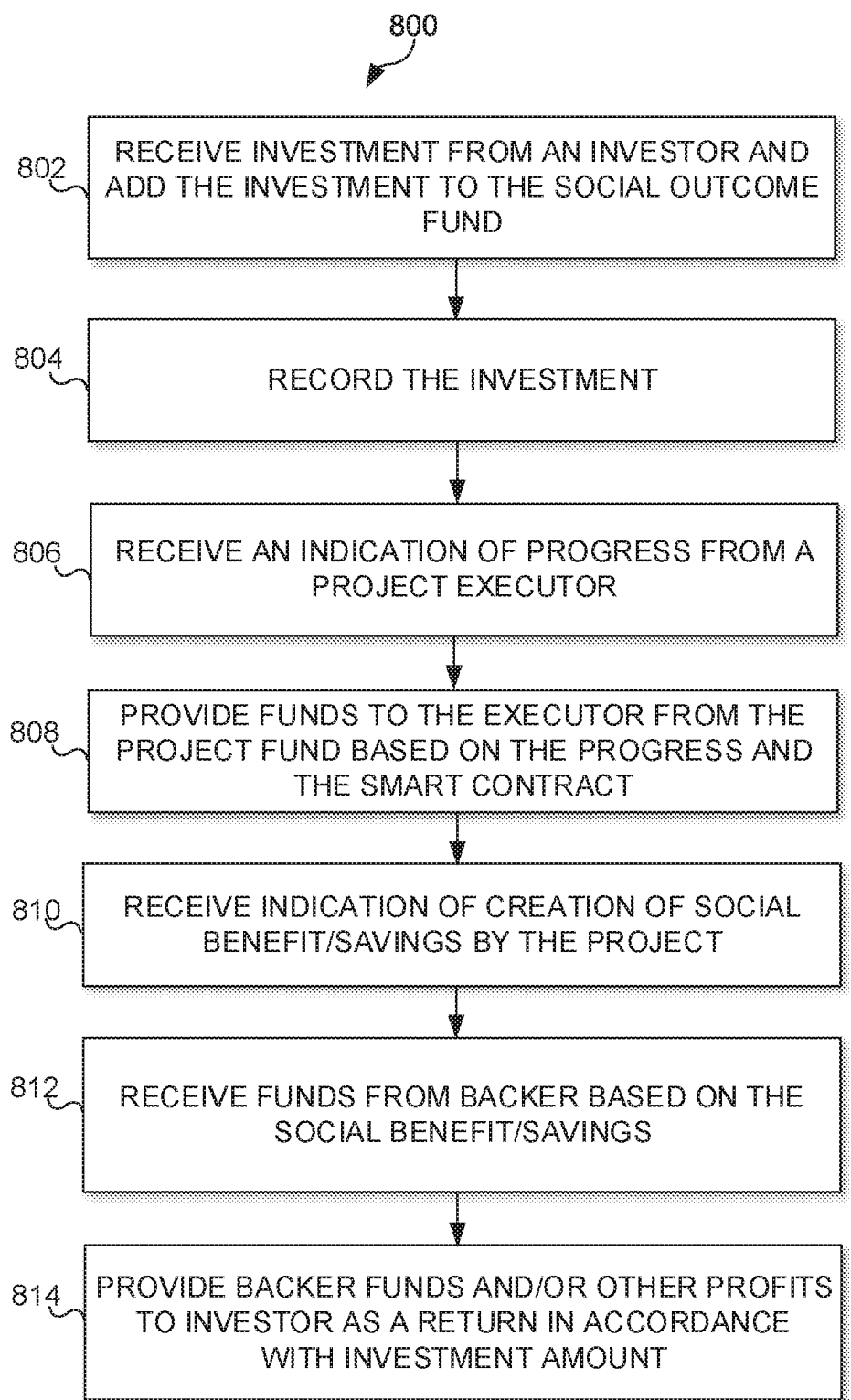
FIG. 8 illustrates an example of a process of implementing a social impact fund, according to an implementation of the disclosure.

FIG. 8 illustrates an example of a process 800 of implementing a social impact fund, according to an implementation of the disclosure.

In an operation 802, process 800 may include receiving an investment from an investor. Operation 802 may include adding the investment to the SOF 105.

In an operation 804, process 800 may include recording the investment. For instance, an amount of the investment may be recorded so that a share of any returns may be provided to the investor based on the amount. In some instances, a particular social impact project is recorded for implementations in which an investor wishes to invest in a particular project. In some instances, an indication of whether all or portion of the investment should be considered a donation may be recorded for tax purposes (and to later distribute the returns back to the SOF 105 instead of the donor), and/or as a convertible grant.

In an operation 806, process 800 may include receiving an indication of progress (such as starting a project or milestone, or completion of a milestone or project) from an executor 120.

In an operation 808, process 800 may include providing funds to the executor 120 from the SOF 105 based on the progress.

In an operation 810, process 800 may include receiving an indication of social benefit or savings created by the project.

In an operation 812, process 800 may include receiving funds from the backer(s) 130 based on the created benefit or savings. Alternatively or additionally, operation 812 may include receiving profits, royalties, or other funds from the executor 120. For example, the executor 120 may have commercialized a product or service as a result of the project and may have agreed to provide at least a portion of the proceeds from such commercialization back to the SOF 105 in exchange for having funded the project.

In an operation 814, process 800 may include providing backer funds, profits, and/or other gains relating to the project to the investor based on the investment amount from the investor. It should be noted that multiple investors may be provided with pro rata returns based on their respective investments in the SOF 105.

As described herein, tokens 103 may be referred to in terms of units or numbers of tokens. However, it should be noted that any such description is not intended to mean an integer number. Rather, a number or value of tokens 103 may relate to a fraction, a measure of value in another currency such as fiat currency, and/or other quantification of value.

The various components of system 100 described herein, such as server 106, nodes 109, and devices that execute the various wallets (111, 121, 131) may include one or more physical processors that are programmed by computer program instructions. Furthermore, the various instructions may be co-located within a single processing unit or, in implementations in which processor(s) 812 may each include multiple processing units, may be distributed and executed at multiple processing units. The various instructions described herein may be stored in a storage device, which may comprise random access memory (RAM), read only memory (ROM), network-based "cloud" memory, other memory, or a combination thereof. The storage device may store the computer program instructions (e.g., the aforementioned instructions) to be executed by the processor(s) as well as data that may be manipulated by the processor(s). The storage device 814 may comprise hard disks, optical disks, tapes, or other storage media for storing computer-executable instructions, data, or both.

Various data such as project parameters, information about various parties, other data, or a combination thereof may be stored in one or more databases off-blockchain (i.e., not on the decentralized ledger 140). For example, in some implementations, all or some of the various data described herein may be stored and represented via tokens (e.g., for which a record may be stored in a decentralized ledger). The various databases may be, include, or interface to, for example, an Oracle™ relational database sold commercially by Oracle Corporation. Other databases, such as Informix™, DB2 or other data storage, including file-based, or query formats, platforms, or resources such as OLAP (On Line Analytical Processing), SQL (Structured Query Language), a SAN (storage area network), Microsoft Access™ or others may also be used, incorporated, or accessed. The database may comprise one or more such databases that reside in one or more physical devices and in one or more physical locations. The database may include cloud-based storage solutions. The database may store a plurality of types of data, files, or both, and associated data or file descriptions, administrative information, or any other data. The various databases may store predefined data, customized data, or both, as described herein.

In other implementations, all or some of the various data described herein may be securitized without tokens using one or more securitization techniques now known or future developed, for example, an iteration of the social outcomes fund described in FIG. 7 and FIG. 8, wherein shares in the fund are transacted off-chain. Off-chain implementations of the various data described herein may also be non-securitized.

Figure 9:
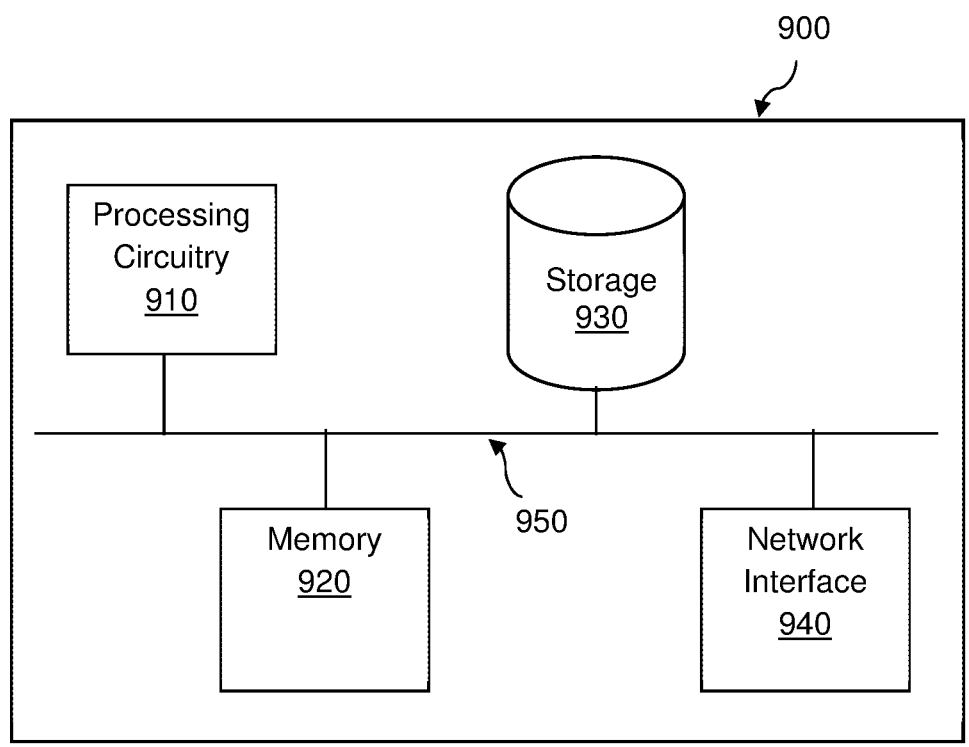
FIG. 9 is an example schematic diagram of a system utilized according to various disclosed embodiments.

FIG. 9 is an example schematic diagram of a system 900 utilized according to various disclosed embodiments. The system 900 includes a processing circuitry 910 coupled to a memory 920, a storage 930, and a network interface 940. In an embodiment, the components of the system 900 may be communicatively connected via a bus 950.

The system 900 may be utilized in accordance with various disclosed embodiments. As an example, the system 900 may store a smart contract (e.g., the smart contract 101, FIG. 1), encode a smart contract, or both. When the system 900 stores a smart contract, the system 900 is configured to execute the processes encoded in the self-executing code of the smart contract, thereby enforcing the smart contract. In an example implementation, the components of the system 900 may be included in the social outcome server 106, FIG. 1.

The processing circuitry 910 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 920 may be volatile (e.g., RAM, etc.), non-volatile (e.g., ROM, flash memory, etc.), or a combination thereof.

In one configuration, software for implementing one or more embodiments disclosed herein may be stored in the storage 930. In another configuration, the memory 920 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 910, cause the processing circuitry 910 to perform the various processes described herein.

The storage 930 may be magnetic storage, optical storage, and the like, and may be realized, for example, as flash memory or other memory technology, CD-ROM, Digital Versatile Disks (DVDs), or any other medium which can be used to store the desired information.

The network interface 940 allows the system 900 for purposes such as, but not limited to, recording transactions on the blockchain network.

It should be understood that the embodiments described herein are not limited to the specific architecture illustrated in FIG. 9, and other architectures may be equally used without departing from the scope of the disclosed embodiments.

The various components illustrated in the Figures may be coupled to at least one other component via a network, which may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, another network, or a combination thereof. In FIG. 1, as well as in other drawing Figures, different numbers of entities than those depicted may be used. Furthermore, according to various implementations, the components described herein may be implemented in hardware, software that configure hardware, or a combination thereof.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for tokenization of social good via blockchain, comprising:
    encoding a smart contract based on a plurality of project parameters for a social impact project, wherein the smart contract includes at least one self-executing code; and
    issuing a token to a user based on an investment made by the user, wherein issuing the token to the user further comprises recording a first transaction on a blockchain indicating that the user owns the token;
    distributing the blockchain across a plurality of nodes in a blockchain network such that the at least one self-executing code is stored across the plurality of nodes;
    recording at least one third transaction on the blockchain, wherein recording each of the at least one third transaction further comprises generating a transaction specifying progress on the social impact project and broadcasting the generated transaction as one of the at least one third transaction to the blockchain network;
    recording, via the at least one self-executing code, at least one second transaction on the blockchain based on the plurality of project parameters and the at least one third transaction recorded on the blockchain, wherein each second transaction includes a respective transfer of funds via the token issued to the user.

2. The method of claim 1, wherein the at least one third transaction indicates at least one milestone of the social impact project that has been achieved, wherein each of the at least one milestone corresponds to one of the at least one self-executing code.

3. The method of claim 1, further comprising:
    adding the investment made by the user to a social outcome fund, wherein the first transaction further indicates the addition of the investment made by the user to the social outcome fund.

4. The method of claim 3, wherein the social outcome fund includes an equity security model, wherein the equity security model defines a plurality of increments of the social outcome fund, wherein the token further indicates at least one of the plurality of increments issued to the user.

5. The method of claim 1, wherein the token has a value backed by at least one external entity, wherein a value of each of the at least one external entity is not affected by the smart contract.

6. The method of claim 1, wherein the social impact project includes repurposing of at least one drug.

7. The method of claim 6, wherein the at least one drug includes a plurality of drugs, wherein the investment made by the user is to a diversified social outcome fund used to fund the repurposing of the plurality of drugs.

8. The method of claim 1, wherein the smart contract is encoded with a plurality of milestones, wherein each of the at least one third transaction includes a milestone identifier, wherein the at least one self-executing code includes instructions for determining whether the milestone identifier of each of the at least one third transaction is a valid milestone of the plurality of milestones.

9. The method of claim 8, wherein each of the plurality of milestones corresponds to exactly one of the at least one self-executing code, wherein the self-executing code corresponding to each milestone includes instructions for validating the milestone.

10. A non-transitory computer readable medium having stored thereon instructions for causing a processing circuitry to execute a process, the process comprising:
    encoding a smart contract based on a plurality of project parameters for a social impact project, wherein the smart contract includes at least one self-executing code; and
    issuing a token to a user based on an investment made by the user, wherein issuing the token to the user further comprises recording a first transaction on a blockchain indicating that the user owns the token;
    distributing the blockchain across a plurality of nodes in a blockchain network such that the at least one self-executing code is stored across the plurality of nodes;
    recording at least one third transaction on the blockchain, wherein recording each of the at least one third transaction further comprises generating a transaction specifying progress on the social impact project and broadcasting the generated transaction as one of the at least one third transaction to the blockchain network;
    recording, via the at least one self-executing code, at least one second transaction on the blockchain based on the plurality of project parameters and the at least one third transaction recorded on the blockchain, wherein each second transaction includes a respective transfer of funds via the token issued to the user.

11. A system for tokenization of social good via blockchain, comprising:
    a processing circuitry; and
    a memory, the memory containing instructions that, when executed by the processing circuitry, configure the system to:
    encode a smart contract based on a plurality of project parameters for a social impact project, wherein the smart contract includes at least one self-executing code; and
    issue a token to a user based on an investment made by the user, wherein issuing the token to the user further comprises recording a first transaction on a blockchain indicating that the user owns the token;
    distributing the blockchain across a plurality of nodes in a blockchain network such that the at least one self-executing code is stored across the plurality of nodes;
    record at least one third transaction on the blockchain, wherein recording each of the at least one third transaction further comprises generating a transaction specifying progress on the social impact project and broadcasting the generated transaction as one of the at least one third transaction to the blockchain network;
    record, via the at least one self-executing code, at least one second transaction on the blockchain based on the plurality of project parameters and the at least one third transaction recorded on the blockchain, wherein each second transaction includes a respective transfer of funds via the token issued to the user.

12. The system of claim 11, wherein the at least one third transaction indicates at least one milestone of the social impact project that has been achieved, wherein each of the at least one milestone corresponds to one of the at least one self-executing code.

13. The system of claim 11, wherein the system is further configured to:
add the investment made by the user to a social outcome fund, wherein the first transaction further indicates the addition of the investment made by the user to the social outcome fund.

14. The system of claim 13, wherein the social outcome fund includes an equity security model, wherein the equity security model defines a plurality of increments of the social outcome fund, wherein the token further indicates at least one of the plurality of increments issued to the user.

15. The system of claim 11, wherein the token has a value backed by at least one external entity, wherein a value of each of the at least one external entity is not affected by the smart contract.

16. The system of claim 11, wherein the social impact project includes repurposing of at least one drug.

17. The system of claim 16, wherein the at least one drug includes a plurality of drugs, wherein the investment made by the user is to a diversified social outcome fund used to fund the repurposing of the plurality of drugs.

18. A method for tokenization of social good, comprising encoding a smart contract based on a plurality of project parameters for a social impact project, wherein the smart contract includes at least one self-executing code; and
issuing a token to a user based on an investment made by the user, wherein issuing the token to the user further comprises recording the investment, wherein each of the at least one self-executing code is configured to provide funds to the user via the token based on the plurality of project parameters and data related to progress of the social impact project, wherein the data related to progress on the social impact project is recorded as at least one progress transaction on the blockchain, wherein each transfer of funds is based on the at least one progress transaction.

* * * * *